(12) United States Patent
Hartl et al.

(10) Patent No.: US 11,903,843 B2
(45) Date of Patent: *Feb. 20, 2024

(54) BIOABSORBABLE IMPLANT COMBINED WITH TISSUE-ENGINEERED COMPOSITE INTERVERTEBRAL DISC

(71) Applicant: Cornell University, Ithaca, NY (US)

(72) Inventors: Roger Hartl, New York, NY (US); Lawrence Bonassar, Ithaca, NY (US); Yu Moriguchi, Forest Hills, NY (US); Gernot Lang, New York, NY (US); Rodrigo Navarro-Ramirez, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/979,917

(22) Filed: Nov. 3, 2022

(65) Prior Publication Data

US 2023/0056877 A1 Feb. 23, 2023

Related U.S. Application Data

(63) Continuation of application No. 16/627,170, filed as application No. PCT/US2018/040445 on Jun. 29, 2018, now Pat. No. 11,504,245.

(Continued)

(51) Int. Cl.
*A61F 2/44* (2006.01)
*A61B 17/70* (2006.01)
(Continued)

(52) U.S. Cl.
CPC .......... *A61F 2/442* (2013.01); *A61B 17/7059* (2013.01); *A61B 2017/00004* (2013.01);
(Continued)

(58) Field of Classification Search
None
See application file for complete search history.

(56) References Cited

U.S. PATENT DOCUMENTS 6,344,058 B1   2/2002  Ferree et al.
8,157,803 B1*  4/2012  Zirkle, Jr. ............ A61B 17/746
                                                606/65

(Continued)

FOREIGN PATENT DOCUMENTS

WO   WO-2010/012025       2/2010
WO   WO-2010012025 A1 *   2/2010  ........... A61K 9/0024

OTHER PUBLICATIONS

Piergiorgia Gentile, et al. "An Overview of Poly(lactic-co-glycolic) Acid (PLGA)-Based Biomaterials for Bone Tissue Engineering", Internal Journal of Molecular Sciences, 2024, pp. 3640-3659.*

(Continued)

*Primary Examiner* — Tessa M Matthews
(74) *Attorney, Agent, or Firm* — FOLEY & LARDNER LLP

(57) ABSTRACT

The present disclosure describes an intervertebral disk replacement system. The system can include a tissue-engineered intervertebral disc that is combined with a bioresorbable stabilization system for structural guidance. The system can prevent or reduce intervertebral disk implant displacement and can increase the stiffness when compared to the implantation of the intervertebral disk implant without the stabilization system.

23 Claims, 4 Drawing Sheets

Related U.S. Application Data

(60) Provisional application No. 62/526,815, filed on Jun. 29, 2017.

(51) Int. Cl.
*A61B 17/00* (2006.01)
*A61F 2/30* (2006.01)

(52) U.S. Cl.
CPC ............ *A61F 2002/30062* (2013.01); *A61F 2002/444* (2013.01); *A61F 2310/00371* (2013.01)

(56) References Cited

U.S. PATENT DOCUMENTS

| | | |
|---|---|---|
| 2002/0016595 A1 | 2/2002 | Michelson |
| 2004/0030342 A1 | 2/2004 | Trieu et al. |
| 2005/0149032 A1 | 7/2005 | Vaughen et al. |
| 2005/0256582 A1 | 11/2005 | Ferree |
| 2006/0082015 A1* | 4/2006 | Happonen .......... A61B 17/7059 264/239 |
| 2007/0168038 A1 | 7/2007 | Trieu |
| 2010/0286781 A1* | 11/2010 | Bullard .............. A61B 17/7059 623/17.11 |
| 2013/0079881 A1 | 3/2013 | Bonassar et al. |

OTHER PUBLICATIONS

International Search Report and Written Opinion in International Patent Application No. PCT/US2018/040445 dated Jan. 9, 2020.
Non-Final Office Action on U.S. Appl. No. 16/627,170 dated Feb. 15, 2022.
Notice of Allowance on U.S. Appl. No. 16/627,170 dated Jul. 21, 2022.

* cited by examiner

BIOABSORBABLE IMPLANT COMBINED WITH TISSUE-ENGINEERED COMPOSITE INTERVERTEBRAL DISC

CROSS-REFERENCE TO RELATED APPLICATION

This application is continuation of U.S. application Ser. No. 16/627,170, filed Dec. 27, 2019, which is a U.S. National Stage of International Patent Application No. PCT/US2018/040445, filed on Jun. 29, 2018, which claims priority to U.S. Provisional Patent Application No. 62/526,815, filed on Jun. 29, 2017, which are incorporated herein by reference in their entireties.

BACKGROUND OF THE DISCLOSURE

Degenerative disc disease (DDD) is among the most common causes of neck and back pain in the adult population, occurring in more than 90% of individuals over the age of 50. While first-line treatments include physical therapy and pharmacologic regimens, surgical intervention is indicated in refractory cases or in severe disease with neurologic compromise. The current standard for surgery in DDD involves complete intervertebral disc (IVD) removal, followed by the placement of an interbody graft for fusion of the adjacent vertebrae. While well tolerated in the majority of patients, fusion carries a significant risk for pseudarthrosis and adjacent segment disease (ASD), which ultimately can lead to reoperations. Alternatively, mechanical disc prostheses can be placed which have the advantage of preserving segmental motion but also alter spine biomechanics leading to ASD. Whether patients are treated through conservative or surgical approaches, the underlying pathophysiology leading to degenerated discs is not addressed.

SUMMARY OF THE DISCLOSURE

The present disclosure describes an intervertebral disk replacement system. The system can include a tissue-engineered intervertebral disc that is combined with a bioresorbable stabilization system for structural guidance. The system can prevent or reduce intervertebral disk implant displacement and can increase the stiffness of a motion segment when compared to the implantation of the intervertebral disk implant without the stabilization system. The bioresorbable stabilization system can guide the intervertebral disk implant through the first weeks after implantation to enhance integration and healing into the host tissue and prevent implant displacement. The stabilization system can degrade over the course of about one year. The stabilization system can be flexible to prevent fusion of the vertebrae neighboring the intervertebral disk implant. The system described herein can provide stability and increases the load distribution on the intervertebral disk implant.

According to at least one aspect of the disclosure, an intervertebral stabilization system can include a tissue-engineered intervertebral disc. The tissue-engineered intervertebral disc is configured to fit within an intervertebral space between a first vertebra and a second vertebra. The tissue-engineered intervertebral disc can include a nucleus pulposus structure comprising a first population of cells. The tissue-engineered intervertebral disc can include an annulus fibrosis structure surrounding and in contact with the nucleus pulposus structure. The system can include a bioresorbable plate to secure the tissue-engineered intervertebral disc between the first vertebra and the second vertebra. The bioresorbable plate is configured to couple with the first vertebra and the second vertebra.

In some implementations, the bioresorbable plate can include a plurality of attachment points to couple the bioresorbable plate with the first vertebra and the second vertebra. In some implementations, the plurality of attachment points is each configured to receive a screw. The screws are bioresorbable. The bioresorbable plate can include 85:15 poly (L-lactide-co-glycolide).

In some implementations, the bioresorbable plate can include a plurality of openings configured to increase the flexibility of the bioresorbable plate. The annulus fibrosis structure can include a second population of cells. The annulus fibrosis structure can include type I collagen.

According to at least one aspect of the disclosure, an intervertebral stabilization method can include providing a bioresorbable stabilization system. The system can include a tissue-engineered intervertebral disc configured to fit within an intervertebral space between a first vertebra and a second vertebra. The tissue-engineered intervertebral disc can include a nucleus pulposus structure comprising a first population of cells. The tissue-engineered intervertebral disc can include an annulus fibrosis structure surrounding and in contact with the nucleus pulposus structure. The method can include implanting the tissue-engineered intervertebral disc between the first vertebra and the second vertebra. The method can include securing, with a bioresorbable plate, the tissue-engineered intervertebral disc between the first vertebra and the second vertebra. The bioresorbable plate can be configured to couple with the first vertebra and the second vertebra.

In some implementations, the bioresorbable plate can include a plurality of attachment points to couple the bioresorbable plate with the first vertebra and the second vertebra. The plurality of attachment points is each configured to receive a screw. The screws can be bioresorbable. The bioresorbable plate can include 85:15 poly (L-lactide-co-glycolide).

The bioresorbable plate comprises a plurality of openings configured to increase the flexibility of the bioresorbable plate. The annulus fibrosis structure can include a second population of cells. The annulus fibrosis structure can include type I collagen.

According to at least one aspect of the disclosure, an intervertebral stabilization kit can include a tissue-engineered intervertebral disc. The tissue-engineered intervertebral disc is configured to fit within an intervertebral space between a first vertebra and a second vertebra. The tissue-engineered intervertebral disc can include a nucleus pulposus structure comprising a first population of cells. The tissue-engineered intervertebral disc can include an annulus fibrosis structure surrounding and in contact with the nucleus pulposus structure. The kit can include a bioresorbable plate to secure the tissue-engineered intervertebral disc between the first vertebra and the second vertebra. The bioresorbable plate can be configured to couple with the first vertebra and the second vertebra. The kit can include a plurality of screws to secure the bioresorbable plate with the first vertebra and the second vertebra.

In some implementations, the screws of the kit are bioresorbable. The bioresorbable plate comprises 85:15 poly (L-lactide-co-glycolide). The bioresorbable plate can include a plurality of openings configured to increase the flexibility of the bioresorbable plate.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
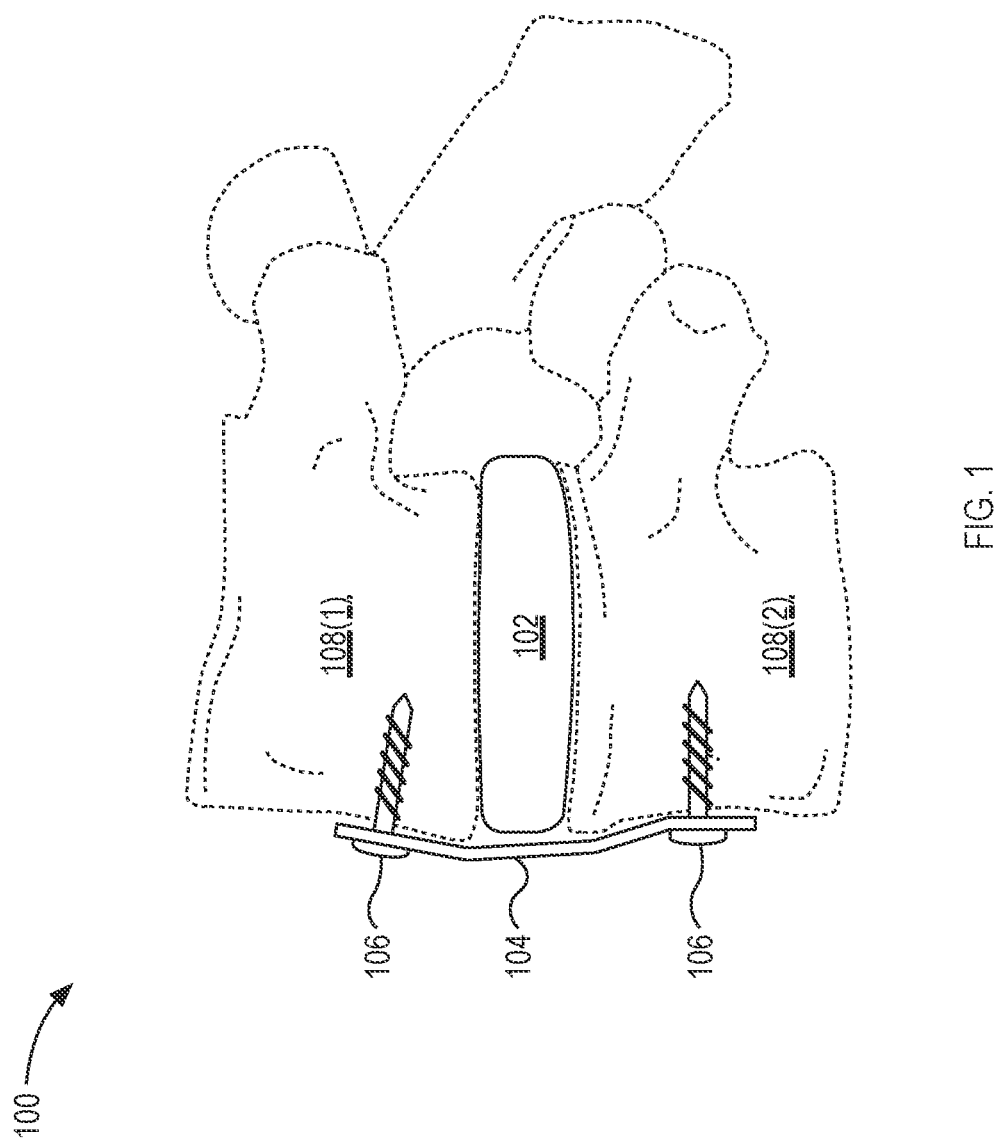
FIG. 1 illustrates an example bioresorbable stabilization system.

FIG. 1 illustrates an example bioresorbable stabilization system 100. The bioresorbable stabilization system 100 includes a tissue-engineered intervertebral disc 102. The bioresorbable stabilization system 100 can include a plate 104 to retain the tissue-engineered intervertebral disc 102 within the intervertebral space between a first vertebra 108(1) and a second vertebra 108(2), which can generally be referred to as vertebrae 108. The plate 104 can be coupled with the vertebrae 108 by screws 106.

The bioresorbable stabilization system 100 can include a tissue-engineered intervertebral disc 102. Below, the tissue-engineered intervertebral disc 102 is described further. As an overview, the tissue-engineered intervertebral disc 102 can be a replacement intervertebral disc that is configured to replace a patient's damaged or diseased intervertebral disc. The tissue-engineered intervertebral disc 102 can include a nucleus pulposus (NP) structure that can include a first population of living cells and an annulus fibrosis (AF) structure that can surround the NP structure. The AF structure can include a second population of living cells and, for example, type I collagen. The collagen fibrils in the AF structure can be circumferentially aligned around the nucleus pulposus region due to cell-mediated contraction in the AF structure. The cells of the NP structure can be seeded into a scaffold, gel, or matrix medium or material.

The bioresorbable stabilization system 100 includes at least one plate 104. The plate 104 is configured to reduce or prevent displacement of the tissue-engineered disc 102. The plate 104 can be coupled ventrally on a cervical canine spinal motion segment. For example, the plate 104 can be coupled with a first vertebra 108(1) and a second vertebra 108(1) and span the intervertebral space therebetween. The plate 104 can control the movement of the bioresorbable stabilization system 100 and the stiffness of the spinal motion segment after implantation.

Figure 3:
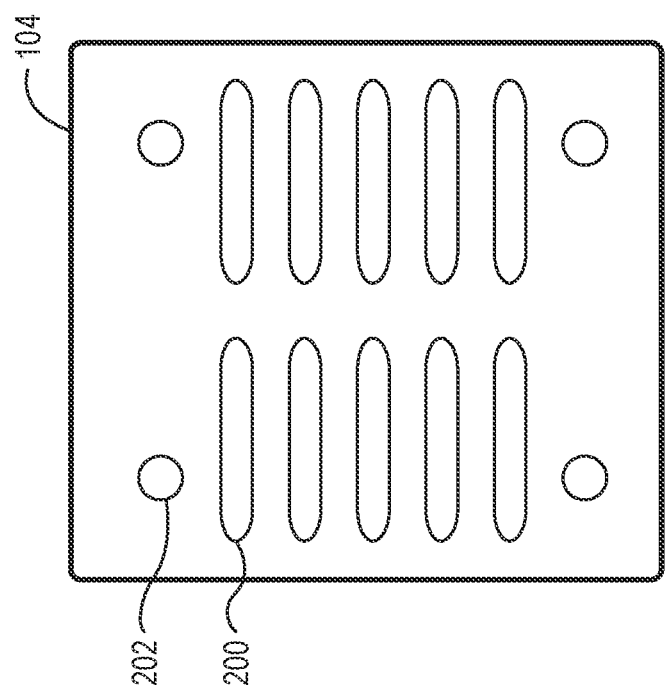
FIGS. 2 and 3 illustrate different views of an example plate that can be used in the system illustrated in FIG. 1.
Figure 2:
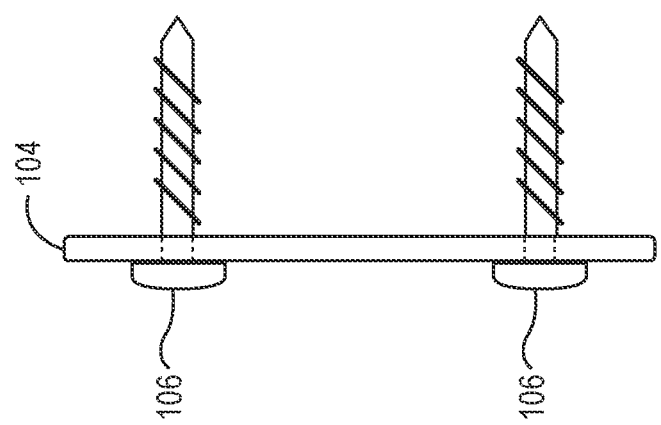

Also referring to FIGS. 2 and 3, which illustrates a side view of the plate 104 and a face view of the plate 104, respectively, the plate 104 can be substantially rectangular or square in shape. In some implementations, the plate 104 can be configured in any other shape. The plate 104 can include rounded edges to reduce trauma that plate 104 causes to tissue near the implantation site.

The plate 104 can include one or more openings 200. The openings 200 can be passages, holes, or cutouts through the body of the plate 104. The openings 200 can increase the flexibility of the plate 104. The openings 200 can enable nutrients and fluids to pass through the plate 104 to, for example, the tissue-engineered intervertebral disc 102 positioned behind the plate 104. The openings 200 can be configured to control the rate at which the plate 104 is absorbed by the patient's body. For example, a solid plate 104 (e.g., a plate 104 without openings 200) can dissolve more slowly than a plate 104 with a plurality of openings 200. In some implementations, the plate 104 can be configured as a mesh.

The plate 104 can include one or more attachment points 202. The plate 104 can include an attachment point 202 near each of the corners of the plate 104. The plate 104 can be secured to the vertebrae 108 at the attachment points 202. In some implementations, the attachment points 202 are cutouts configured to receive a screw 106. In some implementations, the internal surface of the attachment points 202 can be tapped to receive a screw 106. The attachment points 202 can have a diameter between about 1 mm and about 5 mm, between about 1 mm and about 4 mm, between about 1 mm and about 3 mm, or between about 1.5 mm and about 2 mm. The plate 104 can have a thickness between about 0.2 mm and about 3 mm, between about 0.5 mm and about 2 mm, or between about 0.5 mm and about 1 mm.

The plate 104 can be flexible. For example, the plate 104, as illustrated in FIG. 1, can conform to the contours of the vertebrae 108 when secured to the vertebra 108. The plate 104 can be flexible but can provide structural support to the vertebrae 108.

The plate 104 can be resorbable by the patient's body. In some implementations, the patient's body can completely resorb the plate 104 in between about 4 months and about 24 months, between about 6 months and about 18 months, between about 8 months and about 15 months, or between about 10 months and about 12 months. The plate 104 can maintain about 80% of its original strength once implanted for between about 4 weeks and about 16 weeks, between about 6 weeks and about 14 weeks, or between about 8 weeks and about 12 weeks. The length of time that it takes the patient's body to metabolize the plate 104 can be controlled by the dimensions and features of the plate 104. For example, a relatively thicker plate 104 will take longer to lose its structural integrity when compared to a relatively thinner plate 104. In some implementations, the plate 104 can be configured to degrade more quickly by including relatively more openings 200 in the plate 104. The increased number of openings 200 can decrease the amount of material that the needs to be degraded and can also increase the exposed surface area of the plate 104. The increase in surface area can enable a larger portion of the plate 104 to be exposed to fluid that can degrade the plate 104.

The plate 104 can include 85:15 poly (L-lactide-co-glycolide) or poly-lactic acid. The patient's body can resorb the plate 104 to degrade or dissolve the plate 104 over time. For example, over time, fluid can penetrate the material of the plate 104 and through hydrolysis the fluid can break the chemical bonds along the backbone of the polymer chains to produce shorter polymer chains. As the molecular weight of the polymer decreases, the structural integrity of the plate 104 can also decrease. Once the plate 104 has degraded into substantially small particles, the particles can be ingested and digested by the cells of the patient's body. The plate 104 can be broken into lactic and glycolic acids, which the patient's body can eliminate.

In some implementations, as illustrated in FIG. 1, the bioresorbable stabilization system 100 can include a single plate 104. The single plate 104 can be coupled with the ventral surface of the vertebrae 108. In some implementations, the bioresorbable stabilization system 100 can include a plurality of plates 104. For example, the bioresorbable stabilization system 100 can include a plurality of plates 104 that are configured as strips. The strip-based plates 104 can be secured across the intervertebral space around the body of the vertebrae 108. The one or more plates 104 can wrap around between about 10% and 100%, between about 10% and about 80%, between about 10% and about 60%, between about 10% and about 40%, or between about 20% and about 40% of the vertebra 108 body.

The bioresorbable stabilization system 100 can include a plurality of screws 106. The screws 106 can be manufactured from the same material as the plate 104. In some implementations, the patient's body can completely resorb the screws 106 in between about 4 months and about 24 months, between about 6 months and about 18 months, between about 8 months and about 15 months, or between about 10 months and about 12 months. The screws 106 can maintain about 80% of their original strength once implanted for between about 4 weeks and about 16 weeks, between about 6 weeks and about 14 weeks, or between about 8 weeks and about 12 weeks. In some implementations, the screws 106 can be configured to degrade at a slower rate or over a longer period of time when compared to the plate 104. For example, the plate 104 can be configured to degrade and dissolve before the screws 106 such that a relatively large portion of the plate 104 does not become dislodged from the vertebrae 108.

The screws 106 can have a diameter between about 1 mm and about 5 mm, between about 1 mm and about 4 mm, between about 1 mm and about 3 mm, or between about 1.5 mm and about 2 mm. The screws 106 can have a length between about 2 mm and about 10 mm, between about 3 mm and about 8 mm, between about 4 mm and about 8 mm, or between about 6 mm and about 8 mm.

In some implementations, the screws 106 are self-drilling or self-tapping. For example, the screws 106 do not need to be drilled into a pilot or other hole that is first drilled into the vertebra 108. In some implementations, the screws 106 must be screwed into a pre-drilled hole in the vertebra 108

Figure 4:
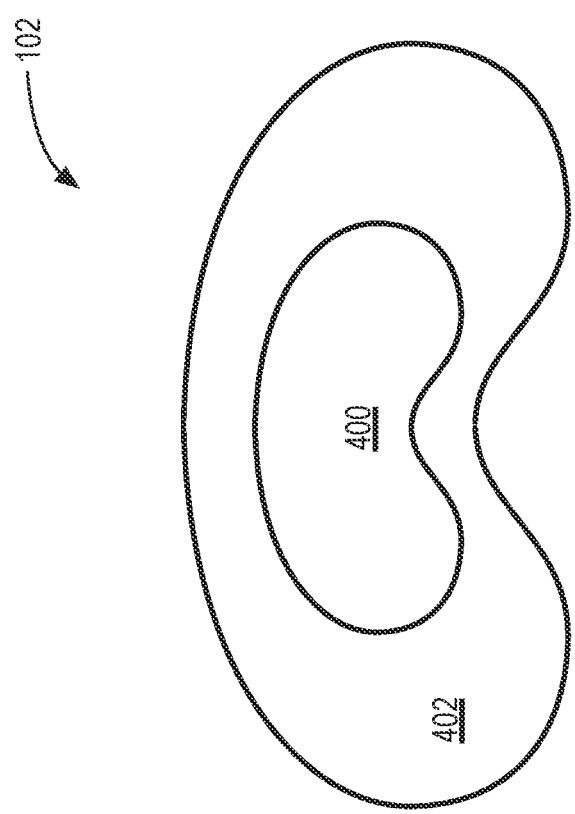
FIG. 4 illustrates a top view of an example tissue-engineered intervertebral disc for use in the system illustrated in FIG. 1.

FIG. 4 illustrates a top view of an example tissue-engineered intervertebral disc 102 for use in the system 100 illustrated in FIG. 1. The tissue-engineered intervertebral disc 102 can be a composite structure that can include an NP structure 400 surrounded by an AF structure 402. The NP structure 400 can include a first population of living cells. The tissue-engineered intervertebral disc 102 can include an AF structure 402 that can surround the NP structure 400. The AF structure 402 can include a second population of living cells.

In some implementations, the NP structure 400 can include the first population of living cells, which can secrete a hydrophilic protein. The AF structure 402 can include type I collagen in addition to the second population of cells.

In some implementations, the population of cells in the NP structure 400 and/or the AF structure 402 can be seeded into a scaffold, gel, or matrix medium or material. For example, the cells may be present in a gel, such as a hydrogel. The hydrogel can include an organic polymer (natural or synthetic) and can be solidified to create a three-dimensional open-lattice structure that entraps molecules of water or other solution to form a gel. The solidification can occur, e.g., by aggregation, coagulation, hydrophobic interactions, or cross-linking hydrogels can rapidly solidify to keep the cells evenly suspended within a mold (or around or within another solidified gel) until the gel solidifies. Hydrogels can be biocompatible (e.g., not toxic to cells suspended in the hydrogel). The hydrogel can include (1) hydrogels cross-linked by ions, e.g., sodium alginate; (2) temperature dependent hydrogels that solidify or set at body temperature; (3) hydrogels set by exposure to either visible or ultraviolet light, e.g., polyethylene glycol polylactic acid copolymers with acrylate end groups; or (4) hydrogels that are set or solidified upon a change in pH.

Examples of materials that can be used to form these different hydrogels include polysaccharides such as alginate, polyphosphazenes, and polyacrylates, which are crosslinked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

In some implementations, the NP structure 400 can include the population of cells in an alginate gel. The alginate gel can include about 3% (w/v) alginate. In some implementations, the alginate gel can include about 0.5% to about 10% (w/v) alginate. In some implementations, the cells of the NP structure 400 can be contained in a gelatin.

The NP structure 400 can include nucleus pulposus cells. The nucleus pulposus (and/or annulus fibrosis) cells can be isolated from any suitable mammalian source organism, including, without limitation, human, simian, orangutan, monkey, chimpanzee, dog, cat, rat, mouse, horse, cow, pig, and the like. In some implementations, the tissue-engineered intervertebral disc 102 can include intervertebral disc stem cells.

In some implementations, cells in the first population of cells can secrete the hydrophilic protein proteoglycan. The cells of the NP structure 400 can also secrete other proteins typically found in the extracellular matrix produced by the cells of an in vivo NP structure. Other hydrophilic proteins may also be secreted in addition to, or alternatively to, proteoglycan. These proteins can bind water molecules to provide compressible properties to the nucleus pulposus. Suitable hydrophilic proteins may include one or more of chondroitin sulfate, heparan sulfate, keratan sulfate, and hyaluronic acid.

The tissue-engineered intervertebral disc 102 can also include the AF structure 402. The AF structure 402 can surround the NP structure 400. The AF structure 402 can include a population of living cells that can be seeded into a gel, matrix, or scaffold, to provide a medium for structure and cell maintenance and growth. The AF structure 402 can include type I collagen. The collagen fibrils in the annulus fibrosus structure can be circumferentially aligned around the NP structure 400 as a result of cell-mediated contraction in the AF structure 402.

In some implementations, the AF structure 402 can include collagen gels seeded with annulus fibrosus cells. Constructs of varying structure and heterogeneity may be created to mimic the circumferential alignment of a native intervertebral disk. In some implementations, circumferential alignment may be induced within gels by contracting annular gels around an inner boundary using either, e.g., a polyethylene center or an alginate center to create the composite structure of the tissue-engineered intervertebral disc 102.

The annulus fibrosus structure may contain type I collagen at a concentration of about 1 to about 5 mg/ml, at a concentration of about 2.5 to about 5 mg/ml, at a concentration of about 1 to about 30 mg/ml, or at a concentration of about 2.5 to about 30 mg/ml. In a further embodiment, the annulus fibrosus structure comprises type I collagen at a concentration of about 1 mg/ml, about 2 mg/ml, about 2.25 mg/ml, about 2.5 mg/ml, about 3 mg/ml, about 3.5 mg/ml, about 4 mg/ml, about 4.5 mg/ml, or about 5 mg/ml.

Additional details regarding the tissue-engineered intervertebral disc 102 can be found in U.S. Pat. No. 9,044,335, which is hereby incorporated by reference in its entirety.

In some implementations, the components of the bioresorbable stabilization system 100 can be components of a kit. The kit can be a sterilized kit. The kit can include a tissue-engineered intervertebral disc 102, one or more plates 104, and a plurality of screws 106 to secure the plate 104 to the vertebrae 108. In some implementations, the kit does not include the tissue-engineered intervertebral disc 102. For example, the kit can include the plate 104 and a plurality of screws 106. In some implementations, the kit can include one or more accessories for the implantation of the bioresorbable stabilization system 100. The accessories can include a screwdriver, handle and screwdriver bit, a handle and drill bit, extra screws 106, and scalpels. In some implementations, the tissue-engineered intervertebral disc 102 can be a component of a second kit.

Figure 5:
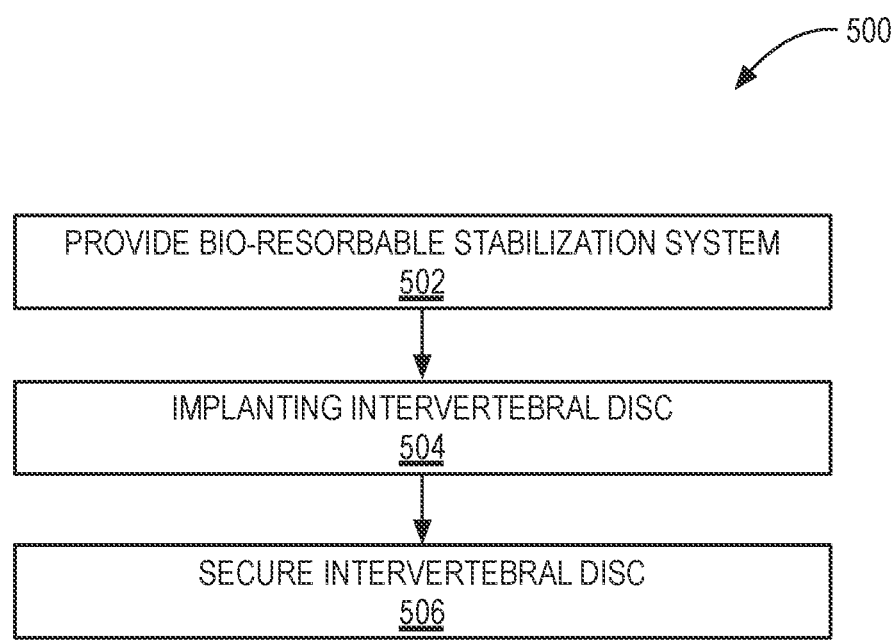
FIG. 5 illustrates a block diagram of an example method to implant a bioresorbable stabilization system.

FIG. 5 illustrates a block diagram of an example method 500 to implant a bioresorbable stabilization system. The method 500 can include providing a bioresorbable stabilization system (step 502). The method 500 can include implanting the tissue-engineered intervertebral disc (step 504). The method 500 can include securing the tissue-engineered intervertebral disc (step 506).

As set forth above, the method 500 can include providing a bioresorbable stabilization system (step 502). Also referring to FIG. 1, among others, the bioresorbable stabilization system 100 can include a tissue-engineered intervertebral disc 102, one or more plates 104, and a plurality of screws 106. In some implementations, the bioresorbable stabilization system 100 can be provided in one or more kits. The tissue-engineered intervertebral disc 102 can be provided in a first kit and the plate 104 and screws 106 can be provided in a second kit. The tissue-engineered intervertebral disc 102 can be a composite structure. For example, the tissue-engineered intervertebral disc 102 can include an NP structure 400 and an AF structure 402. Each of the NP structure 400 and the AF structure 402 can include a different population of cells.

The method 500 can include implanting the tissue-engineered intervertebral disc (step 504). Before implanting the tissue-engineered intervertebral disc 102, a surgeon can perform a discectomy to remove a patient's native intervertebral disk. The surgeon can implant the tissue-engineered intervertebral disc 102 in the void formed from the removal of the native intervertebral disk. The void can be the intervertebral space between a first vertebra 108 and second vertebra 108. The surgeon can implant the tissue-engineered intervertebral disc 102 into the intervertebral space from the patient's ventral side.

The method 500 can include securing the tissue-engineered intervertebral disc (step 506). The surgeon can secure the tissue-engineered intervertebral disc 102 with a plate 104. For example, the surgeon can secure the plate 104 to the vertebra 108 on either side of the intervertebral space into which the tissue-engineered intervertebral disc 102 was implanted. The surgeon can secure the plate 104 to the vertebrae 108 with a plurality of screws 106. The plate 104 and the screws 106 can be configured to degrade over a predetermined amount of time.

EXAMPLES

Experiments were conducted where a tissue-engineered intervertebral disc, such as the tissue-engineered intervertebral discs described herein, was implanted into an animal model. The bioresorbable stabilization system 100 was ventrally implanted into a cervical canine spinal motion segment. The experiments illustrate that the bioresorbable stabilization system 100 prevented displacement of the tissue-engineered intervertebral disc 102 and increased the stiffness of the spinal motion segment.

The cells that were seeded into the tissue-engineered intervertebral disc 102, were harvested from the lumbar spines of skeletally mature beagles. The native intervertebral disks were dissected out of the segments. The native intervertebral disks were washed in Dulbecco's PBS (Gibco BRL) and then separated into the AF and NP regions. To isolate the component cells of each of the regions, tissues was dissected into small pieces and digested in 200 mL of 0.3% wt/vol collagenase type II at 37° C. for 9 h for AF tissue and 6 h for NP tissue. Digested tissue was filtered through 100 μm nylon mesh (BD Biosciences) and centrifuged at 936 g for 7 min. Cells were counted and seeded at 2,500 cells/cm$^2$ in culture flasks with Ham's F-12 media (Gibco BRL) that contained 10% vol/vol fetal bovine serum, 100 units/mL of penicillin (Gemini Bio Products, 100 μg/mL streptomycin, 250 ng/mL amphotericin B, and 25 μg/mL ascorbic acid. Cells were cultured at 37° C., 5% vol/vol $CO_2$, and normoxia to confluence with media changes every 3 days. At confluence, the cells were removed from flasks with 0.05% wt/vol trypsin (Gibco BRL) and counted with a hemocytometer. The cells were then seeded into the tissue-engineered intervertebral discs 102.

To generate the tissue-engineered intervertebral discs 102, T2 weighted MRI images and μCT images were obtained for cervical 4/5 disc levels in the beagle. The T2 weighted MRI images are imported in DICOM format to slicOmatic v4.3 (TomoVision, Magog) and the NP was manually segmented and converted to point cloud images of the NP region. The point cloud images were converted to surface and solid models in Studio 4.0 (Geomagic Inc.). This process resulted in a model containing the dimensions and shape of the NP region. The μCT images were converted to DICOM format and imported into slicOmaticv4.3 (TomoVision) where the boney surfaces of the vertebral bodies were segmented to obtain the overall shape and dimensions of the cervical 4/5 disc space.

The μCT-derived dimensions of the disc space were then combined with the MRI-derived NP model to obtain the target dimensions of the tissue-engineered intervertebral disc 102. A tissue-engineered intervertebral disc 102 of the target dimensions was created. Then 6-8 MRI-derived NP surface and solid models were transferred into SolidWorks to create an injection mold of NP region. The injection mold was 3D printed in acrylonitrile butadiene styrene plastic on an FDM 3,000 machine (Stratasys). Three percent (wt/vol)

low viscosity grade alginate (FMC BioPolymer) seeded with $25 \times 10^6$ NP cells/mL is mixed with 0.02 g/mL $CaSO_4$ (Sigma-Aldrich) to crosslink the alginate, and injected into the NP mold. Cell-seeded alginate NP is then removed from molds and placed in the center of a well of a 24 well plate. Collagen type I was obtained from rat-tail tendon (Sprague Dawley, 7-8-wk old) (Pel-Freez Biologicals). One or two milligrams per millileter collagen gel solution seeded with $1 \times 10^6$ AF cells/mL is subsequently poured and gelled around the alginate NP. The tissue-engineered intervertebral disc 102 were cultured for 4 weeks in previously described media while collagen gel contracted around alginate NP to the proper AF dimensions.

To test the tissue-engineered intervertebral discs, skeletally mature beagles were sacrificed in accordance with Institutional Animal Care and Use Committee (IACUC) guidelines and whole cervical spines were dissected. Individual motion segments from C3/4, C4/5, C5/6, and C6/7 were further dissected using a combination of scalpels, Leksell rongeurs, Kerrison rongeurs, pituitary rongeurs, and handsaws.

Each segment was composed of half of the corresponding vertebral bodies, as well as an intact superior endplate, native IVD, and inferior endplate. The mechanical compatibility was assessed for each motion segment under four different conditions: (1) intact (e.g., before removal of the native intervertebral disk), (2) after discectomy, (3) after implantation of the tissue-engineered intervertebral disc 102, and (4) after implantation of the tissue-engineered intervertebral disc 102 that was secured with the plate 104 and screws 106. Total discectomies were performed by sharp dissection along the IVD/endplate interface followed AF/NP extraction with pituitary rongeurs and preservation of the posterior longitudinal ligament. The tissue-engineered intervertebral discs 102 were inserted into the empty intervertebral disc space with fine atraumatic forceps.

The plate 104 was secured at the ventral midline of each segment with 2 screws 106, one in each of the superior and inferior vertebral bodies. The motion segments were fixed by a clamp at the inferior vertebral body, which was mounted in an ELF 3200 mechanical testing frame (EnduraTec) with a small impermeable platen mounted above. Each construct was surrounded in a gauze soaked with PBS and protease inhibitor (Roche Diagnostics, Indianapolis, IN) to prevent degradation of the disc during testing.

Comparing the stiffness of the motion segment under each of the test conditions (e.g., intact, discectomy, tissue-engineered intervertebral disc 102 only, and tissue-engineered intervertebral disc 102 secured with a plate 104) provided that the tissue-engineered intervertebral disc 102 secured with the plate 104 provided a 1.9-fold increase in stiffness when compared to the tissue-engineered intervertebral disc 102 only.

This example illustrates that the bioresorbable stabilization system 100 can be used to help stabilize a cervical motion segment. The bioresorbable stabilization system 100 can enable load sharing to the tissue-engineered intervertebral disc 102. The implantation of the tissue-engineered intervertebral disc 102 by itself can result in a relatively similar mechanical properties to those of the discectomized segments, which can suggest low magnitudes of loads are shared by the construct. The significant increase in stiffness due to the plate 104 can suggests that the plate 104 can increases the stability of tissue-engineered intervertebral disc 102 construct. The tissue-engineered intervertebral disc 102 can help reduce implant displacement outside of the disc space.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts, and those elements may be combined in other ways to accomplish the same objectives. Acts, elements, and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations, elements, or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. An intervertebral stabilization system, comprising:
   a tissue-engineered intervertebral disc configured to fit within an intervertebral space between a first vertebra and a second vertebra;
   a bioresorbable plate, comprising a plurality of openings, to secure the tissue-engineered intervertebral disc between the first vertebra and the second vertebra, wherein the bioresorbable plate is configured to couple with the first vertebra and the second vertebra via at least some of the plurality of openings; and
   a plurality of bioresorbable screws to secure the bioresorbable plate to the first vertebra and the second vertebra via the at least some of the plurality of openings, wherein the plurality of bioresorbable screws are configured to degrade at a slower rate or over a longer period of time relative to the bioresorbable plate.

2. The system of claim 1, wherein the bioresorbable plate is configured as a mesh with a second plurality of openings.

3. The system of claim 1, wherein the plurality of openings is a first set of openings for receiving the plurality of bioresorbable screws to secure the bioresorbable plate to the first vertebra and the second vertebra, and wherein the bioresorbable plate further comprises a second set of openings configured to enable nutrients and fluids to pass through the bioresorbable plate to the tissue-engineered intervertebral disc positioned behind the bioresorbable plate.

4. The system of claim 1, wherein the tissue-engineered intervertebral disc comprises a nucleus pulposus structure comprising a population of cells.

5. The system of claim 4, wherein the tissue-engineered intervertebral disc further comprises an annulus fibrosis structure surrounding and in contact with the nucleus pulposus structure.

6. The system of claim 5, wherein the annulus fibrosis structure comprises a second population of cells.

7. The system of claim 6, wherein the population of cells is different from the second population of cells.

8. The system of claim 6, wherein at least one of the population of cells and the second population of cells comprises living cells.

9. The system of claim 5, wherein the annulus fibrosis structure comprises type I collagen.

10. The system of claim 5, wherein the annulus fibrosis structure comprises collagen, and wherein collagen fibrils in the annulus fibrosis structure are circumferentially aligned around the nucleus pulposus structure due to cell-mediated contraction in the annulus fibrosis structure.

11. The system of claim 1, wherein the bioresorbable plate comprises 85:15 poly (L-lactide-co-glycolide).

12. The system of claim 1, wherein the plurality of openings comprises a first opening and a second opening, wherein the first opening is separated from the second opening by a distance greater than the intervertebral space between the first vertebra and the second vertebra to configure the bioresorbable plate to be secured across the intervertebral space between the first vertebra and the second vertebra, and wherein the plurality of bioresorbable screws comprises a first screw configured to be received through the first opening and a second screw configured to be received through the second opening to couple the bioresorbable plate with the first vertebra and the second vertebra and thereby retain the tissue-engineered intervertebral disc within the intervertebral space.

13. The system of claim 1, wherein the plurality of openings is a first set of openings, and wherein the bioresorbable plate further comprises a second set of openings configured to increase the flexibility of the bioresorbable plate.

14. The system of claim 1, wherein the tissue-engineered intervertebral disc comprises a nucleus pulposus structure and an annulus fibrosis structure surrounding and in contact with the nucleus pulposus structure, wherein the annulus fibrosis structure comprises collagen, and wherein collagen fibrils in the annulus fibrosis structure are circumferentially aligned around the nucleus pulposus structure.

15. An intervertebral stabilization method, comprising:
   obtaining a bio-resorbable stabilization system comprising a tissue-engineered intervertebral disc configured to fit within an intervertebral space between a first vertebra and a second vertebra;
   implanting the tissue-engineered intervertebral disc between the first vertebra and the second vertebra; and
   securing, with a bioresorbable plate and a plurality of bioresorbable screws, the tissue-engineered intervertebral disc between the first vertebra and the second vertebra, wherein the bioresorbable plate comprises a plurality of openings configured to receive the plurality of bioresorbable screws to couple the bioresorbable plate with the first vertebra and the second vertebra, and wherein the plurality of bioresorbable screws are configured to degrade at a slower rate or over a longer period of time relative to the bioresorbable plate.

16. The method of claim 15, wherein the tissue-engineered intervertebral disc comprises a nucleus pulposus structure comprising a population of cells.

17. The method of claim 16, wherein the tissue-engineered intervertebral disc further comprises an annulus fibrosis structure surrounding and in contact with the nucleus pulposus structure.

18. The method of claim 15, wherein the bioresorbable plate is configured as a mesh with a second plurality of openings.

19. The method of claim 15, wherein the tissue-engineered intervertebral disc comprises a nucleus pulposus structure and an annulus fibrosis structure surrounding and in contact with the nucleus pulposus structure, wherein the annulus fibrosis structure comprises collagen, and wherein collagen fibrils in the annulus fibrosis structure are circumferentially aligned around the nucleus pulposus structure.

20. An intervertebral stabilization kit, comprising:
a tissue-engineered intervertebral disc configured to fit within an intervertebral space between a first vertebra and a second vertebra;
a bioresorbable plate to secure the tissue-engineered intervertebral disc between the first vertebra and the second vertebra, wherein the bioresorbable plate comprises a plurality of openings; and
a plurality of bioresorbable screws configured to be received in the plurality of openings and thereby to secure the bioresorbable plate with the first vertebra and the second vertebra, wherein the plurality of bioresorbable screws are configured to degrade at a slower rate or over a longer period of time relative to the bioresorbable plate.

21. The intervertebral stabilization kit of claim 20, wherein the bioresorbable plate is configured as a mesh with a second plurality of openings.

22. The intervertebral stabilization kit of claim 20, wherein the tissue-engineered intervertebral disc comprises a nucleus pulposus structure comprising a first population of cells, and an annulus fibrosis structure surrounding and in contact with the nucleus pulposus structure, wherein the annulus fibrosis structure comprises a second population of cells.

23. The intervertebral stabilization kit of claim 20, wherein the tissue-engineered intervertebral disc comprises a nucleus pulposus structure and an annulus fibrosis structure surrounding and in contact with the nucleus pulposus structure, wherein the annulus fibrosis structure comprises collagen, and wherein collagen fibrils in the annulus fibrosis structure are circumferentially aligned around the nucleus pulposus structure.

\* \* \* \* \*